United States Patent [19]

Ernst

[11] Patent Number: 5,659,125

[45] Date of Patent: Aug. 19, 1997

[54] AUTOMATIC CALIBRATION METHOD FOR CARBON MONOXIDE MONITORS

[75] Inventor: Stephen M. Ernst, Colorado Springs, Colo.

[73] Assignee: Nighthawk Systems, Inc., Colorado Springs, Colo.

[21] Appl. No.: 474,309

[22] Filed: Jun. 7, 1995

[51] Int. Cl.⁶ ........................... G01N 1/22
[52] U.S. Cl. ............. 73/1.03; 364/571.04; 364/571.05; 73/1.07
[58] Field of Search ............. 73/1 G, 1 R; 364/571.01, 364/571.02, 571.04, 571.05

[56] References Cited

U.S. PATENT DOCUMENTS

| | | |
|---|---|---|
| 4,151,738 | 5/1979 | Hyer et al. ............................. 73/1 G |
| 4,348,732 | 9/1982 | Kreft .................................... 73/1 G |
| 4,481,804 | 11/1984 | Eberhard et al. ...................... 73/1 G |
| 4,489,592 | 12/1984 | Pacanowski et al. .................. 73/1 G |
| 5,060,505 | 10/1991 | Tury et al. ............................. 73/1 G |

*Primary Examiner*—Hezron E. Williams
*Assistant Examiner*—Nashmiya Ashraf
*Attorney, Agent, or Firm*—Dorr, Carson, Sloan & Birney, P.C.

[57] ABSTRACT

A method and apparatus to automatically calibrate a carbon monoxide detector placed in an environment having a known concentration of carbon monoxide. The monitor is placed in a calibration mode in which it reads the output signal from the sensor and normalizes the output signal to a convenient scale. The normalized reading is used to compute a calibration coefficient. The calibration coefficient is stored in a non-volatile memory integrated with the carbon monoxide monitor.

9 Claims, 4 Drawing Sheets

AUTOMATIC CALIBRATION METHOD FOR CARBON MONOXIDE MONITORS

BACKGROUND OF THE INVENTION

1. Field of the Invention

The present invention relates, in general, to calibration of electronic instruments, and, more particularly, to a method and system for automatically calibrating digital carbon monoxide sensors.

2. Statement of the Problem

Carbon monoxide monitors are an increasingly popular consumer safety device. Unlike common smoke detectors, burglar alarms, and even simple carbon monoxide detectors, a carbon monoxide monitor senses and reports the value of carbon monoxide concentration rather than merely triggering an alarm once a hazard condition exists. Thus, the carbon monoxide monitor is more akin to a measurement device that the common smoke detector or burglar alarm. As in any measurement device, calibration is critical so that accurate values are reported to the user.

Carbon monoxide monitors continuously measure levels of carbon monoxide in the environment. Sources of carbon monoxide include automobiles, fireplaces, gas appliances, and other devices that combust hydrocarbon fuels. Because carbon monoxide cannot be detected by smell or taste, accurate detection is important.

Unfortunately, moderate background levels of carbon monoxide exist in most environments. To distinguish harmful levels of carbon monoxide from the background, it is necessary to have an accurate measurement of the carbon monoxide level. This measurement is typically represented in parts per million (ppm). Acceptable background levels may be as high as 25–35 ppm. Harmful exposure occurs, however, at only slightly higher concentrations of 75–100 ppm over a period of a few hours. Hence, accurate measurements of carbon monoxide concentration are critical to the task of distinguishing background CO levels from harmful exposure levels.

Carbon monoxide monitors are based around some form of sensor that produces an electrical signal (i.e., a change in resistance, capacitance, oscillation frequency, optical reflectance, transmission, or the like) in response to changes in carbon monoxide concentration. A variety of CO sensors are known and are commercially available. Sensors vary significantly from unit-to-unit in their sensitivity and offset properties. Sensitivity refers to the rate of change in output signal in response to changing levels of carbon monoxide. Offset refers to the sensor output signal when no carbon monoxide is present. In order to accurately measure CO using these sensors, the unit-to-unit differences must be compensated for in a process of calibrating the carbon monoxide monitor in which the CO sensors are installed.

Carbon monoxide monitors have traditionally been used in industrial environments. Because of this, they were low volume, relatively expensive products. Because they were not mass-marketed in the consumer marketplace, manufacturers had the luxury of calibrating each device manually since the high cost of manual calibration could be passed on to the purchaser. Prior calibration processes involved placing the CO monitor in an environment having a known concentration of CO (i.e., 100 ppm), and adjusting the monitor until it generated a correct output signal. The adjustments typically involved varying resistor or capacitor values connected to the CO sensor, or by changing the gain of amplifiers coupled to read the sensor output signal.

Another problem with manual calibration is that is often cost prohibitive to recalibrate the CO monitor as the circuits age. CO sensors often change in sensitivity and offset over time resulting in degraded performance with age. Manual calibration costs are a significant portion of a consumer CO monitor that sells for $100 or less. Occasionally calibration must be performed more than one time to rework monitors during manufacture, further increasing the cost of manual calibration. What is needed is an automatic method for calibrating carbon monoxide monitors that requires minimal human intervention to achieve accurate, reproducible results.

3. Solution to the Problem

The above problems are solved by a carbon monoxide monitor with an integrated automatic calibration circuit. Because the calibration circuit allows the carbon monoxide monitor to calibrate itself when placed in an environment with a known concentration of carbon monoxide, manual involvement in the calibration process is substantially eliminated. By limiting the cost of calibration, less expensive CO monitors are available and CO monitors can be cost effectively recalibrated as they age. Further, automatic calibration results in a level of calibration accuracy difficult to achieve with manual calibration in a production environment.

SUMMARY OF THE INVENTION

Briefly stated, the present invention involves a method to automatically calibrate a carbon monoxide detector placed in an environment having a known concentration of carbon monoxide. The monitor is placed in a calibration mode in which it reads the output signal from the sensor and normalizes the output signal to a convenient scale. The normalized reading is used to compute a calibration coefficient. The calibration coefficient is stored in a non-volatile memory integrated with the carbon monoxide monitor.

Another aspect of the present invention provides a carbon monoxide monitor with automatic calibration capability. The carbon monoxide detector includes a sensor providing a sensor output signal that is an electrical signal responsive to carbon monoxide concentration. A programmable processing circuit receives the sensor output signal. A user operable switch is coupled to the processing circuit and places the monitor in a calibration mode. The processing circuit is programmed to compute the calibration coefficient from the sensor output signal when the calibration mode is detected from the user operable switch. The processing circuit is coupled to a non-volatile memory and programmed to write-enable the memory only when the calibration mode is detected. The processing circuit stores the calibration coefficient in the non-volatile memory during the calibration mode, then read the calibration coefficient from the non-volatile memory when in normal operating mode.

DETAILED DESCRIPTION OF THE DRAWING

1. Overview.

The present invention is adapted to provide a method and apparatus for calibrating a batch of carbon monoxide monitors (i.e., more than one) with minimal manual intervention.

By calibrating a large number at the same time, calibration costs are reduced. By minimizing human intervention during the calibration process calibration costs are reduced and higher accuracy can be obtained. Further, automatic calibration speeds the process of calibration further lowering the cost.

While the calibration method and apparatus in accordance with the present invention are illustrated and described in terms of a carbon monoxide monitor, it should be apparent that any monitor or measurement tool requiring a low cost, accurate calibration routine could make use of the teachings of the present invention. It is recognized that the carbon monoxide monitor market is unique and that it is a consumer device expected to provide near-laboratory accuracy at costs well below typical laboratory instruments. It is expected, however, that as environmental monitoring concerns increase in the consumer marketplace that a great variety of instruments will require and benefit from the automatic calibration method and apparatus, or its equivalence, as taught by the present invention.

Figure 1:
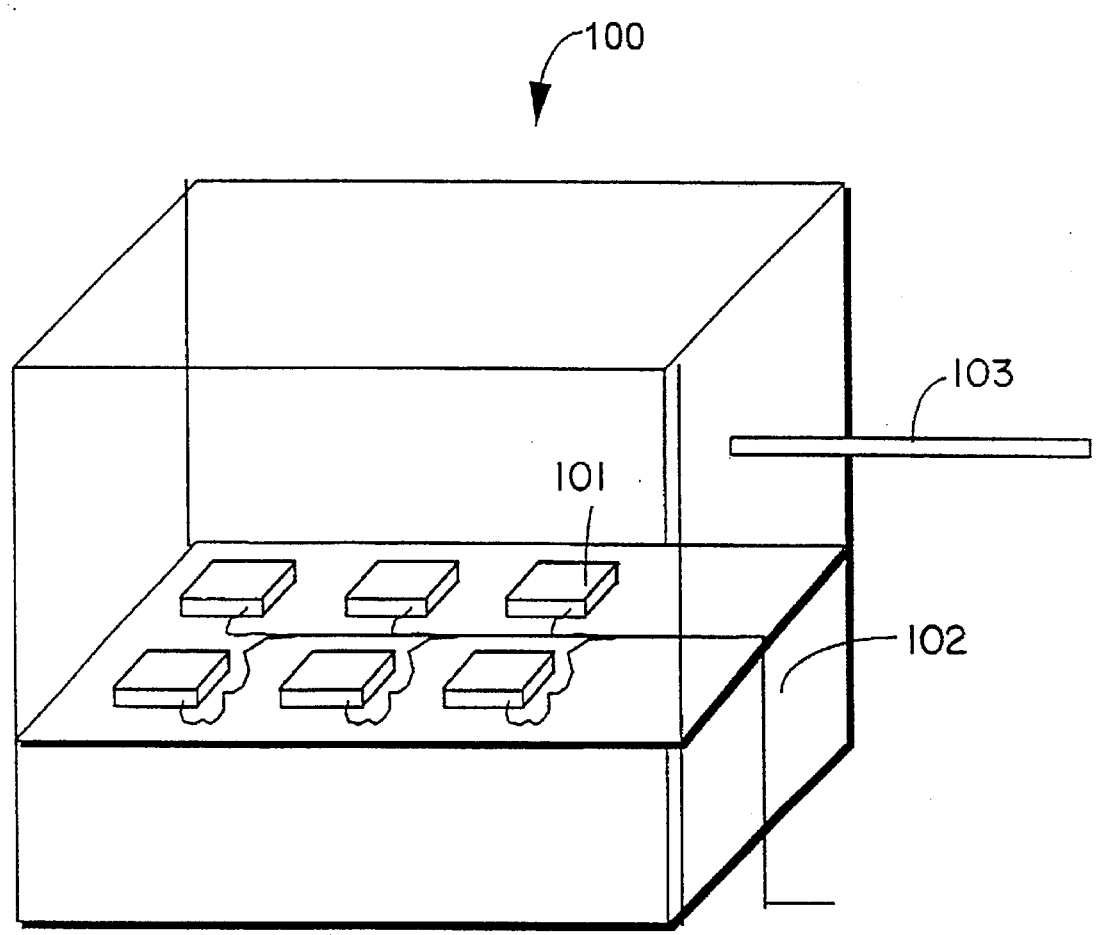
FIG. 1 is a schematic representation of a measurement system capable of automatic calibration in accordance with the method of the present invention.

Calibration of a measurement apparatus is typically performed by placing the measurement apparatus in a known environment that has a carefully controlled or monitored concentration of carbon monoxide. As shown in FIG. 1, a plurality of carbon monoxide monitors 101 are placed in a calibration chamber 100. A known quantity or concentration of carbon monoxide is supplied to calibration chamber 100 by gas supply 103. An exhaust system (not shown) would usually be supplied to calibration chamber 100 also to prevent gas escape while chamber 100 is being loaded or unloaded. A concentration of carbon monoxide in chamber 100 is carefully controlled or monitored by a precision instrument to ensure a known, fixed level.

Monitors 101 may be calibrated at one or more concentration levels. For example, monitors 101 may be calibrated at concentrations of 50 ppm and 200 ppm. The selection of how many levels the calibration routine of the present invention should be performed depends on the linearity of the output from each sensor within carbon monoxide detectors 101. The sensor output will be most accurate at the point at which the monitor is calibrated and will deviate somewhat from complete accuracy between calibration points. In a preferred embodiment, sensors 101 are calibrated at a single concentration of 200 ppm that is believed to provide sufficient accuracy.

2. Carbon Monoxide Detector with Automatic Calibration.

Figure 2:
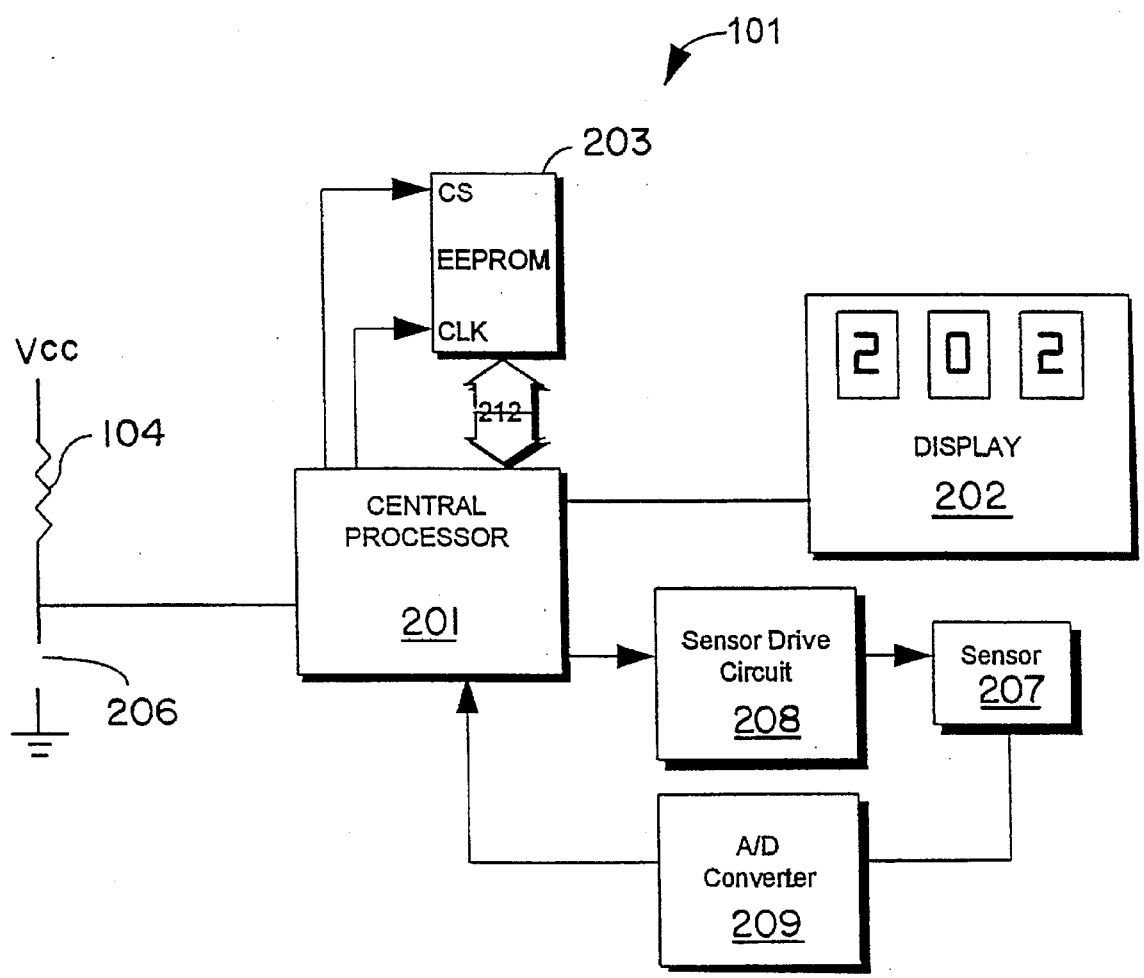
FIG. 2 is a simplified representation of a calibration chamber for performing automatic calibration in accordance with the method of the present invention.

FIG. 2 shows schematically components of a sensor having automatic calibration capability in accordance with the present invention. Conventional circuitry such as power supplies, display drivers, clocks, and the like that are not necessary for a complete understanding of the present invention are not illustrated in FIG. 2 for ease of description. In FIG. 2, each of the key components are illustrated as separate blocks, but it should be understood that these functional blocks could be integrated in one or more physical devices using known semiconductor manufacturing techniques. The particular level of integration selected by the user will be driven primarily by cost and manufacturing constraints. Accordingly, variations of the present invention merely involve rearrangement or integration of key components described herein are considered equivalent to the present invention.

Sensor 207 is a carbon monoxide sensor that produces an electrical output signal coupled analog-to-digital (A/D) converter 209 in response to changes in carbon monoxide exposure. Sensor 207 is driven by sensor drive circuit 208 that provides a current and/or voltage stimulus to sensor 207. Sensor drive 208 may also drive heating, cooling, or other similar auxiliary components to sensor 207 control the environment of sensor 207 in an attempt to minimize variability of the output from sensor 207. The sensor output signal is an analog signal that is converted by A/D converter 209 to a digital signal and provided to central processor 201. Central processor 201 also provides control signals to sensor drive circuit 208.

Central processor 201 is a digital logic processor capable of executing a stored set of instructions and capable of performing basic math operations such as addition. In a preferred embodiment, central processor 201 is implemented in a programmable microcontroller having an integrated program memory, registers, and an arithmetic logic unit. Central processor 201 could be implemented in a hardware programmed controller such as a programmable logic device, or applications specific integrated circuit (ASIC).

Central processor 201 receives the digital input from A/D converter 209. The signal provided by sensor 207 is a raw or uncalibrated reading. Hence, the digital signal provided by A/D converter 209 is a raw, uncalibrated digital representation of the reading from sensor 207. Central processor calibrates the raw reading and in a preferred embodiment displays the calibrated or corrected reading on display 202.

Display 202 is preferably a digital display using a plurality of seven-segment LCD or LED display elements. The advantage of a digital display is that it presents more information to the user on actual concentration levels to which the user is exposed. As set out hereinbefore, a disadvantage of the digital display is that it requires increased accuracy as it does little good to provide three digits of information to the user if the information is not accurate to three digits. Alternatively, a simpler display may be provided having merely an alarm or signal light to indicate carbon monoxide concentration levels. Even where a simpler display is used, however, the calibration method in accordance with the present invention provides low cost accurate operation of central processor 201 in computing the alarm limits that must be signaled to the user.

In accordance with the present invention, central processor 201 can be placed in a calibration mode by placing a Jumper across the open leads shown at 206 in FIG. 2. When 206 is open, node 211 is at a logic high because it is coupled to the power supply voltage VCC through resistor 204. With a jumper in place across junction 206, node 211 is pulled to a logic low as voltage is dropped across resistor 204. The jumper arrangement shown in FIG. 2 for signaling a calibration mode to central processor 201 is merely an example of any of a number of known switching or signaling circuits capable of signaling calibration mode to central processor 201. It is desirable that whatever switch mechanism is used to indicate calibration mode to central processor 201 is substantially non-volatile so that power can be removed from monitor 101 while the unit is place in calibration chamber 100 (shown in FIG. 1). In this manner, when power is applied monitor 101 immediately enters calibration mode without further manual intervention.

In calibration mode, central processor 201 accepts the digital sensor signal from A/D converter 209 and computes one or more calibration coefficients. Calibration coefficients are constants that are particular to each monitor 101 that allow central processor 201 to compute an accurate reading from the digitized raw reading provided by A/D converter 209. In essence, central processor 201 scales the raw reading provided by A/D converter 209 so that the corrected value used for computing alarms and displaying on display 202 represent true readings of carbon monoxide concentration.

In calibration mode, central processor 201 calculates the calibration coefficients and stores them in EEPROM 203. EEPROM 203 is merely an example of a non-volatile memory that is useful for storing the calibration coefficients in accordance with the method and apparatus of the present invention. Any convenient type of non-volatile memory that is easily integrated into carbon monoxide monitor 101 can be used. Central processor 201 provides data and instructions to EEPROM 203 over bus 212. Bi-directional bus 212 also provides data from EEPROM 203 to central processor 201 during normal operation.

Central processor 201 provides clock signals to the CLK input of EEPROM 203. The clock signals are pulses indicating when data is to be clocked in from bus 212 into EEPROM 203. Typical EEPROMs require instructions to clear or write data as well as to address locations in the EEPROM 203. Simpler non-volatile memory circuits may require little instruction and possibly eliminate the need for the CLK connection to central processor 201. Central processor 201 is also coupled to the chip select (CS) input of EEPROM 203. The chip select input simply enables EEPROM 203 so that it can be addressed for writing or reading data over bus 212. An important feature of the present invention is that only in calibration mode can EEPROM 203 be write enabled. That is to say, data can only be written to EEPROM 203 when in calibration mode as signaled by a jumper across leads 206. This is accomplished by appropriate programming in central processor 201 that checks for the presence of the jumper across leads 206 before allowing a write instruction across bus 212. Where EEPROM 203 has a write enable input, the signal can be provided directly by coupling leads 206 or node 211 shown in FIG. 2 to the EEPROM write enable input(not shown). In this manner, the calibration constants can only be written to EEPROM 203 during calibration mode so that during normal operation the calibration constants are protected from alteration or erasure.

During normal operation the jumpers are removed from leads 206 as shown in FIG. 2. During normal operation, central processor selects EEPROM 203 and clocks in an appropriate address provided across bus 212 to access the stored calibration constants. The calibration constants are then provided to central processor 201. In one embodiment, central processor 201 multiplies the digital output received from A/D converter 209 by the calibration constant provided across bus 212 to generate the corrected reading. In some cases it may be necessary to subtract or add the calibration constant or offset calibration constant to the digital output from A/D converter 209. Any mathematical manipulation or combination of the calibration constant with the output from A/D converter 209 that is appropriate for a particular monitor 101 is considered equivalent to the method and apparatus in accordance with the present invention.

3. Method of Operation.

Figure 3:
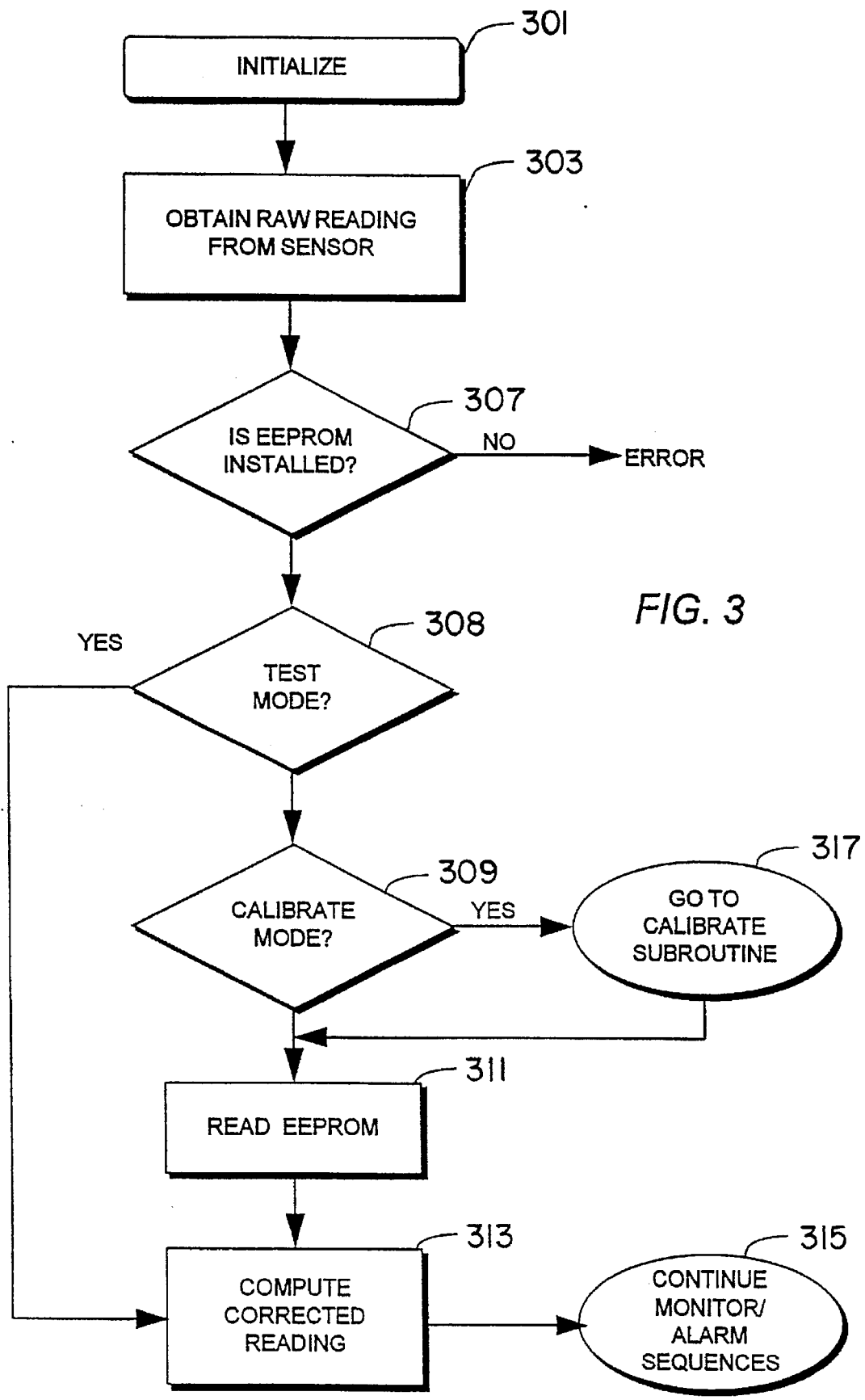
FIG. 3 is a flow diagram illustrating the steps for operating a carbon monoxide monitor having the automatic calibration capability.
Figure 4:
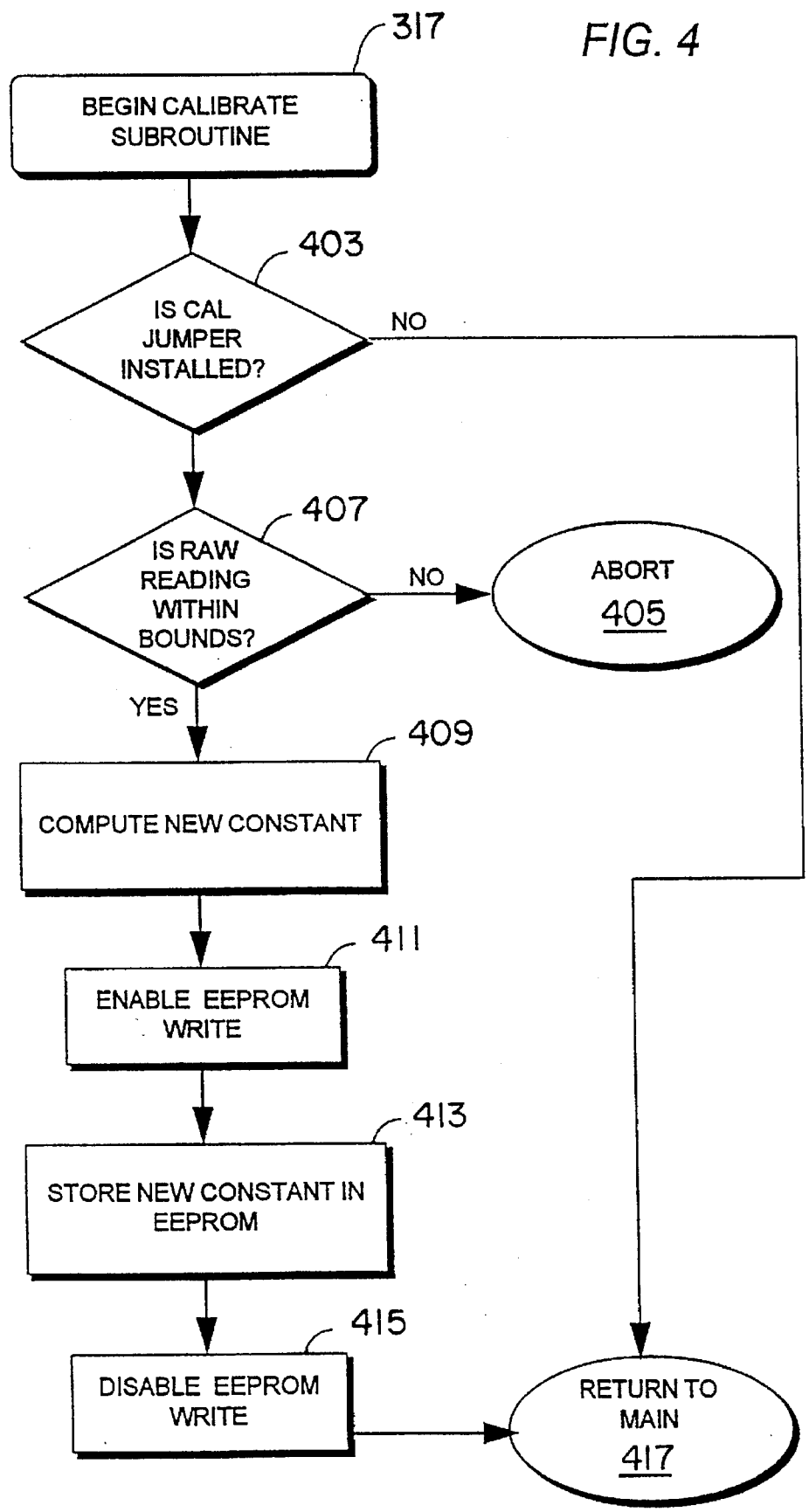
FIG. 4 is a flow diagram of the automatic calibration method in accordance with the present invention.

FIG. 3 and FIG. 4 illustrate in flow diagram form steps in accordance with the method of the present invention. The method is initialized at step 301 by performing various routines to verify operation of subcircuits connected to central processor 201 (shown in FIG. 2) and to set any registers internal to central processor 201 to correct initial values from the random states in which they typically start. In step 303, a raw reading is obtained from sensor 303. Step 303 includes operation of both sensor 207 and A/D converter 209 as well as sensor drive circuit 208 shown in FIG. 2.

In step 307, central processor 201 verifies installation of EEPROM 203 (shown in FIG. 2). If EEPROM 203 is not detected, an error message is generated. If the EEPROM is detected, flow passes to step 308 where central processor 201 checks to see if monitor 101 is in a test mode. If monitor 101 is in test mode, calibration should not be performed and flow passes to step 313 and step 315. It should be understood that the EEPROM check and test mode check shown in steps 307 and 308 are optional depending on the particular hardware configuration of monitor 101. If EEPROM 307 is always installed it is not necessary, but highly recommended, to verify its installation. Failure to detect EEPROM 307 may indicate a hardware functionality problem that should be brought to the attention of the manufacturer or user.

In step 309, central processor 201 verifies that a calibration mode exists. It is important that calibration mode be verified in step 309 by verifying the presence of a jumper across leads 206 shown in FIG. 2. Calibration mode check step 309 allows program control to pass to calibrate subroutine 317. If the calibrate mode is not present, control passes to read EEPROM step 311 in which data is read from EEPROM but EEPROM 203 (shown in FIG. 2) is not enabled for writing. After the EEPROM is read, the corrected reading is computed in step 313 using the stored calibration constants from EEPROM 203. Once the correct reading is computed, the monitor and alarm sequences are continued in step 315. Only when the calibration mode is detected in 309 will flow pass to the calibrate subroutine step 317 that is shown in greater detail in FIG. 4.

In step 403, the presence of the calibration jumper across leads 206 is again verified. This double check of the presence of calibration jumper 206 is an important step in accordance with the present invention in order to prevent writing erroneous data to EEPROM 203. If the calibration jumper is not detected, flow passes to abort sequence 405. Only if the calibration jumper is detected, will flow pass to step 407 in which the raw reading is checked to be within predetermined boundaries. The purpose of the boundary check step 407 is to verify that the output from sensor 207 is reasonably accurate and can be calibrated using the method of the present invention and to verify that monitor 101 has been placed in the calibration chamber 100.

Once it is determined that the raw reading is within bounds, a new calibration constant is computed in step 409. In the preferred embodiment where the control environment within calibration chamber 100 is kept at 200 ppm, the calibration constant can be computed in step 409 by dividing 200 by the raw reading. Once the calibration constant is computed, in step 411 the EEPROM 203 is write enabled by an appropriate instruction clocked in from central processor 201 through bus 212 to EEPROM 203.

Once write enabled, the new constant is stored in an appropriate address in EEPROM 203 during step 413. This requires central processor 201 to clock in the appropriate address across bus 212 into EEPROM 203. Once the appropriate location is addressed, calibration constant is provided by central processor 212 to EEPROM 203 and a write instruction executed. Once the write instruction is executed, EEPROM 203 is write disabled in step 415 to prevent further modification, alteration, or erasure of the calibration constant from EEPROM 203. Flow then returns to the main program in step 417 which is the read EEPROM step 311 shown in FIG. 3.

By now it should be appreciated that a simple method for automatically calibrating a carbon monoxide monitor is provided. Further, a carbon monoxide monitor having automatic calibration capability is provided wherein the monitor is placed in a calibration chamber and automatically compute calibration constants and store them in non-volatile memory. Once removed from the calibration chamber and taken out of calibration mode the calibration constant is accessed to correct raw readings from sensor 107 and to compute erected or scaled readings that are displayed and used for triggering alarms. It will be apparent that many modifications and components, integration, display, and switching are possible of the particular embodiments shown. Accordingly, the present invention is not limited to the particular implementation and embodiments shown and described herein, but encompasses all such apparent modifications and equivalent components and connections.

I claim:

1. A method for calibrating a gas concentration monitor comprising the steps:

placing the monitor in a calibration mode;

providing the monitor with programmed information as to a calibration concentration level;

placing the monitor entirely within an isolated chamber containing gas to be monitored and said gas being at the calibration concentration level;

activating the monitor so that the monitor automatically takes a raw measurement of the concentration of the gas to be monitored;

using the monitor to compare the raw measurement with the programmed calibration concentration level the calculate a calibration constant;

using the monitor to automatically write enable a non-volatile memory integrated with the monitor;

using the monitor to automatically store the calculated calibration constant in the non-volatile memory; and using the monitor to automatically disable the non-volatile memory write capability.

2. The method of claim 1 wherein before the step of automatically write enabling, the monitor verifies that the monitor has been placed in the calibration mode.

3. The method of claim 1 wherein the step of calculating a calibration constant comprises dividing the calibration concentration level by the raw measurement.

4. The method of claim 1 wherein the programmed calibration concentration level is about 200 parts per million carbon monoxide.

5. The method of claim 1 further comprising the steps of:

providing the monitor with programmed information as to a second calibration concentration level;

placing the monitor in an environment at the second calibration concentration level of the gas to be monitored;

activating the monitor so that the monitor automatically takes a second raw measurement of the concentration of the gas to be monitored; and comparing the second raw measurement with the programmed second calibration concentration level to calculate a second calibration constant.

6. A system for calibrating a gas concentration monitor comprising:

an isolated chamber having gas at a known gas concentration;

a support within the isolated chamber for holding the gas concentration monitor entirely within the chamber;

a power supply for providing power to the gas concentration monitor within the isolated chamber;

a gas sensor within the gas concentration monitor for generating a sensor output signal responsive to the gas at the known gas concentration to which the sensor is exposed;

a programmable control circuit within the gas concentration monitor coupled to receive the gas sensor output signal, wherein the control circuit is programmed with data identifying a calibration concentration level; and means for placing the control circuit in a calibration mode in which the control circuit autonomously:

i) takes a reading from the gas sensor, ii) computes a calibration constant from the reading and the programmed calibration concentration level, and iii) stores the calibration constant.

7. The system of claim 6 further comprising a non-volatile memory coupled to the control circuit for storing the calibration constant.

8. The system of claim 6 wherein the control circuit is implemented in a microcontroller.

9. The system of claim 6 wherein the gas sensor is a carbon monoxide sensor.

\* \* \* \* \*